United States Patent [19]

Kirkpatrick

[11] 4,306,018
[45] Dec. 15, 1981

[54] METHOD OF GAS-HEAT EXCHANGE

[75] Inventor: Anthony F. Kirkpatrick, Miami, Fla.

[73] Assignee: The Board of Regents of the University of Nebraska, Lincoln, Nebr.

[21] Appl. No.: 163,329

[22] Filed: Jun. 26, 1980

[51] Int. Cl.³ .............................................. A01N 1/02
[52] U.S. Cl. .............................. 435/2; 261/DIG. 28; 422/46; 422/48
[58] Field of Search ................... 435/2; 422/46, 48; 261/DIG. 28

[56] References Cited
U.S. PATENT DOCUMENTS

| | | | |
|---|---|---|---|
| 2,972,349 | 2/1961 | De Wall | 422/48 |
| 3,489,647 | 1/1970 | Kolobow | 435/2 |
| 3,764,271 | 10/1973 | Brumfield | 422/46 |
| 3,792,978 | 2/1974 | Freedman | 210/321 |
| 3,892,533 | 7/1975 | Freedman | 210/321 |
| 4,138,288 | 2/1979 | Lewin | 435/2 |

*Primary Examiner*—Sam Rosen
*Attorney, Agent, or Firm*—Vincent L. Carney

[57] ABSTRACT

To supply oxygen to blood and control its carbon dioxide content, the blood is pumped through a silicone rubber tube wound as a helix around an aluminum cylinder. In a typical use, water at 37° C. is pumped through the cylinder to maintain the temperature constant and a gas containing 95% oxygen and 5% carbon dioxide is passed over the silicone rubber tube so that: (1) oxygen passes through the rubber silicone tube to enrich the blood in oxygen; and (2) carbon dioxide is exchanged through the silicone rubber tube between the blood and the outside gas.

21 Claims, 4 Drawing Figures

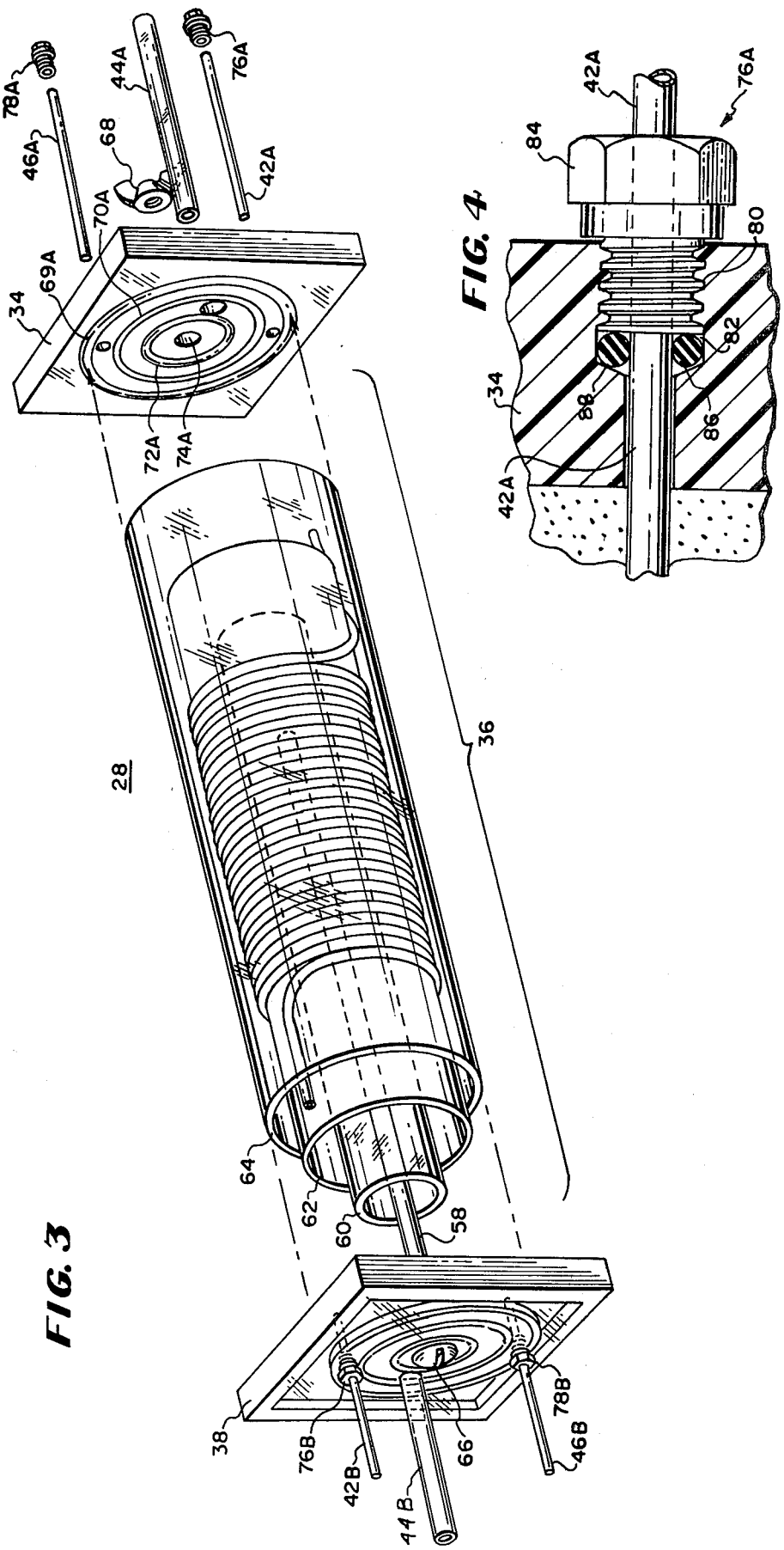

METHOD OF GAS-HEAT EXCHANGE

BACKGROUND OF THE INVENTION

This invention relates to gas-heat exchangers and particularly to gas-heat exchangers that may be used as lungs.

In one class of gas-heat exchanger, a perfusate is controlled in temperature by a heat exchanger and gas is introduced and removed from it through silicone rubber membranes.

In one type of prior art gas-heat exchanger of this class, the temperature of the perfusate is controlled by enclosing the entire perfusion instrument in a temperature-controlled environment. The perfusate passes through silicone rubber tubing that is randomly curved in a jar which contains oxygen.

This type of gas-heat exchanger has several disadvantages, such as: (1) enclosure of the entire perfusion system in a temperature-controlled environment made it difficult to carry out manipulations on the perfused organ; (2) inefficient removal of carbon dioxide due to a large gas compartment; (3) being large and difficult to handle because of the necessity of having a temperature-controlled environment; and (4) being subject to changes in carbon dioxide and oxygen exchange rates with time so that it is not repeatable.

In another type of prior art gas-heat exchanger of this class, the perfusate is passed through a heat exchanger and then through a tube which includes silicone rubber sacks enriched with oxygen. This prior art type of gas-heat exchanger has several disadvantages, such as: (1) being unreliable; (2) not repeatable in the exchange of carbon dioxide and oxygen; (3) being complex; (4) being expensive; (5) requiring separate heat exchangers and gas exchangers; and (6) generally not being reused.

SUMMARY OF THE INVENTION

Accordingly, it is an object of the invention to provide a novel gas-heat exchanger.

It is a further object of the invention to provide a novel method of gas-heat exchange with a liquid.

It is a still further object of the invention to provide a novel lung.

It is a still further object of the invention to provide an integrated gas-heat exchanger.

It is a still further object of the invention to provide a gas exchanger in which the operation is repeatable through several different runs and across a long period of time.

It is a still further object of the invention to provide a gas-heat exchanger which has a relatively small gas compartment.

It is a still further object of the invention to provide a gas-heat exchanger with a surprisingly high rate of exchange of gases for a length of tubing of liquid.

It is a still further object of the invention to provide an economical gas-heat exchanger.

In accordance with the above and further objects of the invention, a perfusate is pumped through a tube formed from a silicone rubber membrane having one surface positioned against the heat exchanger while gas is pumped over another surface of the tube. The tube is within a relatively small compartment, with a portion of the wall of the tube being against a surface of the heat exchanger.

Advantageously, the heat exchanger is a heat conductive cylinder and the silicone rubber membrane is a tube wound in a helix about the cylinder so that its side against the cylinder is controlled in temperature by a liquid flowing through the cylinder. On the opposite side of the cylinder there is a compartment formed between an outer cylinder and the heat exchange cylinder through which a gas such as oxygen may flow.

The gas-heat exchanger has special application to blood as a perfusate when oxygen is pumped through the chamber to introduce oxygen into the blood and remove carbon dioxide while the temperature is maintained at approximately 37° C. by warm water flowing through the cylinder. The cylinder may advantageously be of metal such as aluminum.

From the above description, it can be understood that the gas-heat exchanger of this invention has several advantages such as: (1) it provides surprisingly efficient exchange of gases; (2) it is repeatable in operation for gas-heat exchange for a large number of cycles; (3) it may be steam autoclaved; (4) it is simple in construction and economical; (5) it combines in an integrated unit both the heat exchanger and the gas exchanger; and (6) it has a relatively small gas chamber.

The above noted and features of the invention will be better understood from the following detailed description when considered with reference to the accompanying drawings in which:

FIG. 3 is an exploded perspective view of a portion of the embodiment of FIG. 1; and FIG. 4 is an enlarged, fragmentary, sectional, elevational view of a portion of FIG. 3.

Figure 1:
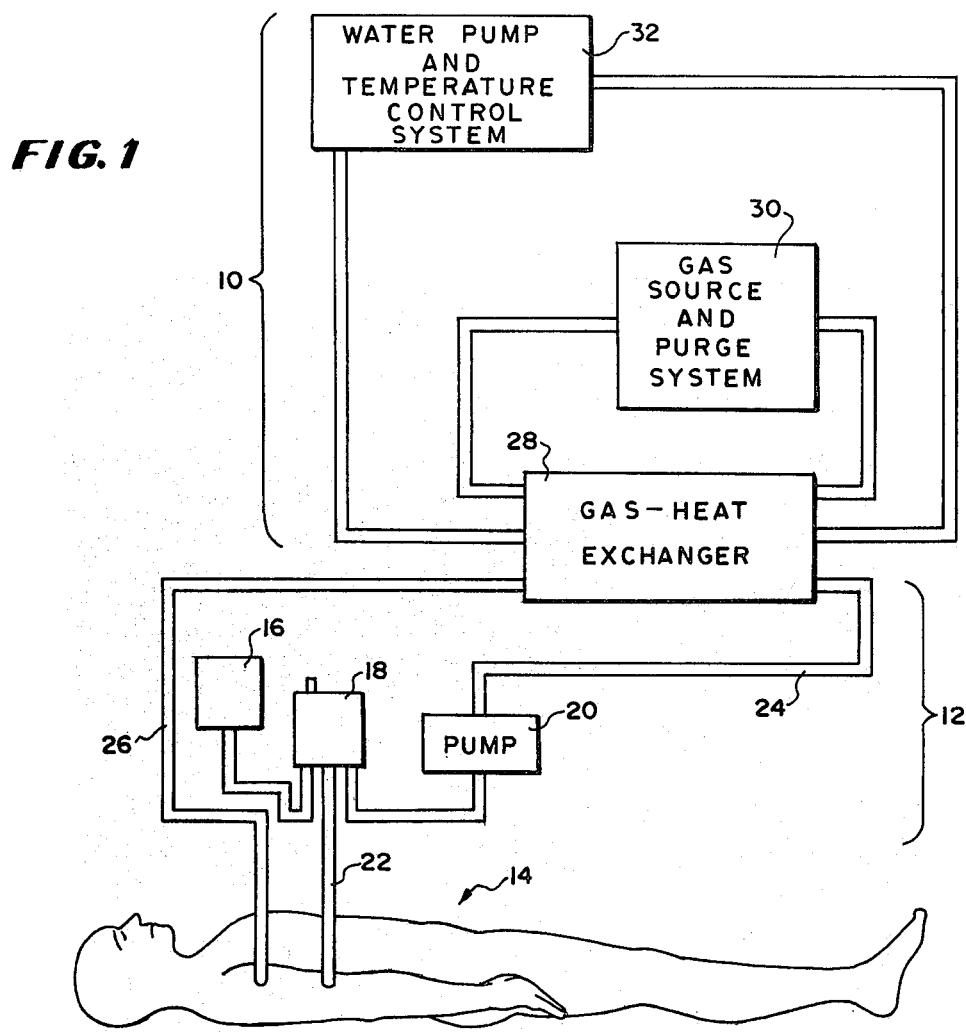
FIG. 1 is a block diagram illustrating a lung in use in accordance with an embodiment of the invention.

In FIG. 1, there is shown a schematic diagram illustrating the lung 10 connected through a utilization system 12 to a patient 14. The utilization system 12 is connected to the patient 14 and the lung 10 and includes a pump 20 pumping blood from the patient 14 to the lung 10 for the removal of carbon dioxide and the addition of oxygen and returning the oxygen rich blood to the patient 14.

Although a lung 10 is shown in FIG. 1 to provide oxygen to the blood of a patient and remove carbon dioxide, the lung of this invention may have other uses such as for the perfusion of organs in a laboratory such as a heart or the like to support its life separate from the intact animal that would normally have the organ. Moreover, while a lung is illustrated to supply oxygen to blood and to remove carbon dioxide, the apparatus may be used to exchange other gases from other liquids.

The utilization system 12 includes a cardiotomy reservoir 16, a venous reservoir 18, and a pump 20. With this system blood is drawn from the veins of a patient 14 through a conduit 22 in the venous reservoir 18 and from the venous reservoir 18 it is pumped by the pump 29 through the conduit 24. Blood in the conduit 24 circulates through the lung 10 where it receives oxygen and releases carbon dioxide. When it leaves the lung 10 it is pumped through the conduit 26 back to the patient 14. The cardiotomy reservoir 16 supplies blood to the heart during this process and the venous compartment 18 provides a blood reservoir and a compartment for the removal of bubbles and foam from the blood.

While a utilization system 12 is shown for supplying blood to the lung 10 from a living patient 14 for oxygenation and for releasing carbon dioxide and returning it to the patient 14, other utilization systems may be used.

For example, blood or salt water or the like may be supplied to an animal organ, which may be a human organ, in the laboratory to study the effects on the animal organ. Moreover, the structure of the utilization system 12 may be other than that shown in FIG. 1 since many such systems are known in the prior art. It will, of course, differ for laboratory use from the systems used with a human subject.

The lung 10 includes a gas-heat exchanger 28, a gas source and purge system 30 and a water pump and temperature control system 32. The conduits 24 and 26 are connected to the gas-heat exchanger 28 in the lung 10 to supply the flow of blood from the conduit 24 through the gas-heat exchanger 28 where its temperature is controlled and it receives oxygen and releases carbon dioxide before flowing back to the patient through the conduit 26.

To supply oxygen to the blood of the patient 14, the gas source and purge system 30 is connected to the gas-heat exchanger 28 with the flow being generally in the opposite direction as the blood and in contact with a membrane for the supplying of oxygen through the membrane to the blood as it flows through the gas-heat exchanger 28. To control the temperature of the blood, the water pump and temperature control system 32 is connected to the gas-heat exchanger 28 through conduits to supply water at 37° C. to gas-heat exchanger 28 with the flow being opposite to the direction of blood.

While the gas source and purge system 30 is described as supplying oxygen it may also supply nitrogen, air or other gases when desirable. Similarly, the water pump and temperature control system 32 may supply other types of temperature control liquids or other types of pumps may supply gases such as nitrogen, air or the like but in the preferred embodiment, it supplies warm water.

In operation, a liquid such as blood is obtained and passed through a gas-heat exchanger where its temperature is controlled while gases are exchanged to remove gases from or add gases to or both add and remove gases to and from the liquid.

To supply a liquid such as blood to the lung 10, the liquid is pumped from the source such as blood from the vein of a patient 14, through the reservoir 18 into the gas-heat exchanger 28 and, after the exchange of gases at a controlled temperature, returned to the patient 14. Other liquids or blood may be used in the laboratory for perfusion of organs of animals including humans by continuously recirculating the fluid rather than removing it from an intact animal and returning it to the animal.

To adjust the temperature and exchange gases in the liquid, the liquid is passed through the conduit 24 through the gas-heat exchanger 28 in one direction through silicone rubber tubing (not shown in FIG. 1) which is supported by a heat exchange support (not shown in FIG. 1). While the fluid passes through the tubing and adjacent to the heat exchange support, a temperature control liquid is pumped through the heat exchange support to maintain its temperature and conduct heat to or from the liquid. At the same time, a gas such as oxygen is brought into contact with another surface of the tubing. In the case of blood, warm water or fluids at different selected temperatures are normally used to adjust the temperature and oxygen is usually the gas on the outside of the silicone rubber tube which causes oxygen to enter the blood and carbon dioxide to leave it.

Figure 2:
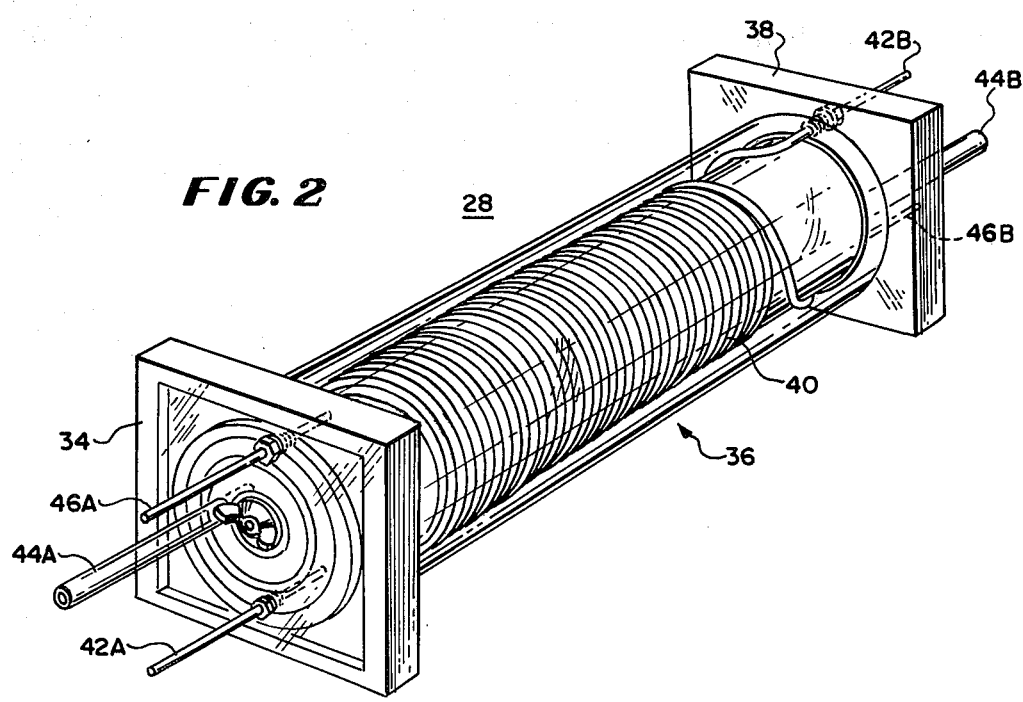
FIG. 2 is a perspective view of a portion of FIG. 1.

In FIG. 2, there is shown a perspective view of the gas-heat exchanger 28 having first and second end plates 34 and 38 respectively and a central gas-heat exchange portion 36. The central gas-heat exchange portion 36 has a silicone rubber tube 40 wound as a helix within it for carrying perfusate while its temperature is controlled and gases are exchanged with the perfusate, with the first and second end plates 34 and 38 sealing opposite ends of the central gas-heat exchange portion 36 and providing ports for temperature control fluids, perfusate and gases.

The first and second end plates 34 and 38 are each right regular parallelepipeds having their larger dimensioned flat surfaces adjacent to the ends of the central gas-heat exchange portion 36 so that their shorter length corners are parallel to the longitudinal axis of the central gas-heat exchange portion 36 and their longer edges are in planes perpendicular to the central gas-heat exchange portion 36.

The first end plate 34 has passing through it a first tubular conduit 42A, a second tubular conduit 44A and a third tubular conduit 46A. Similarly, the second end plate 38 has passing through it a first tubular conduit 42B, a second tubular conduit 44B and a third tubular conduit 46B. The tubular conduits each extend into the central gas-heat exchange portion 36.

To permit the flow of the perfusate, which in the preferred embodiment is blood, the first tubular conduits 42A and 42B are connected to conduits 24 and 26 (FIG. 1) respectively to receive the fluid that is entering the gas-heat exchanger 28. In the preferred embodiment, this is venous blood. The other ends of the first tubular conduits 42A and 42B pass through the end plates 34 and 38 respectively and are connected to opposite ends of the silicone rubber tubing 40 to communicate with its interior so that the perfusate flows through the silicone rubber tubing 40 for control of temperature and exchange of gases, which in the preferred embodiment means the acceptance of oxygen and removal of carbon dioxide while its temperature is maintained at approximately 37° C.

To control the temperature of the perfusate while it is within the central gas-heat exchange portion 36, the second tubular conduits 44A and 44B each have one end connected to a different one of the conduits from the water pump and temperature control system 32 (FIG. 1) to receive fluid at a controlled temperature and opposite ends extending through the first and second end plates 34 and 38 respectively to apply it through a central cylinder in the central gas-heat exchange portion 36.

To increase the temperature transfer, the flow of water through the conduits 44A and 44B is in a direction opposite to the flow of the perfusate within the central gas-heat exchange portion 36 so that the temperature control fluid is pumped into the tubular conduit 44B and exits from the tubular conduit 44A. Also, the conduits 44A and 44B are on diametrically opposite sides of the gas-heat portion 36 to aid in mixing of the fluid. In the preferred embodiment, the fluid is warm water which is maintained at approximately 37° C. to maintain blood at this temperature.

To supply gas to the perfusate and remove other gases, the third tubular conduit 46A and the third tubular conduit 46B are each connected to different ports of the gas source and purge system 30 (FIG. 1) through different conduits. The other ends of the third tubular conduits 46A and 46B extend through the end plates 34 and 38 respectively into the compartment which contains the silicone rubber tubing 40 so that gas supplied to that chamber passes through the wall of the silicone rubber tubing into the perfusate and other gases pass through the wall of the silicone rubber tubing from the perfusate into the chamber to be transported by the flow of gas out of the lung 10.

Gas enters through third tubular conduit 46B and exits through third tubular conduit 46A from the central gas-heat exchange portion 36 to flow in the opposite direction of the perfusate. In the preferred embodiment, the perfusate is blood, oxygen enters the blood and carbon dioxide leaves the blood, being removed from the chamber by the flow of oxygen through the chamber.

In operation, generally the perfusate flows through the gas-heat exchanger 28 (FIG. 1), receiving some gas, releasing other gas and having its temperature controlled as it flows.

The perfusate flows from the first tubular conduit 42A into the central gas-heat exchange portion 36 through the helically coiled silicone rubber tubing 40. As it flows through the tube 40 it flows around an aluminum tube which serves as the heat exchanger within a compartment that serves as the gas exchanger, before exiting through the first tubular conduit 42B.

When the lung 10 was tested in the perfusion of an animal heart, the heart's activity was superior to any previously reported heart under similar perfusion conditions. One explanation of this improved activity is that there is better oxygen transfer because the helical path induces secondary velocities and turbulence and thus increase the exchange of gases and heat. For example, the exchange of gases are greater than it would be for an equivalent length of straight silicone tubing without turns in it which is exposed on all sides of the tube to an oxygen atmosphere.

While the perfusate is flowing through the helical coil of silicone rubber tubing 40, a liquid is flowing through the center of the central gas-heat exchange portion 36 at a constant temperature to control the temperature of the tube upon which the coiled silicone rubber tubing 40 is wound.

The flow of liquid through the center of the tube is in the opposite direction as the flow of perfusate. Similarly, gas flows in the opposite direction relative to the direction of flow of perfusate through the outer chamber where it contacts the top surface of the helically wound silicone tubing for gas exchange and then is removed through the third tubular conduit 46A.

As can be understood from the above description, the gas-heat exchanger 28 has several advantages such as: (1) the tubes are held in place so that they cannot move and change the gas-heat characteristics during use; (2) there may be a superior exchange of gases and heat, probably because of the turbulence and secondary velocities created from the turns in the coiled tube and the counter current flow of gas and temperature control fluids relative to the direction of flow of perfusate; (3) the chamber for gases such as oxygen and carbon dioxide is small and thus provides easy purging and a high concentration of the exchanged gases; (4) the heat transfer mechanism is compact and part of the support mechanism for the gas exchange; and (5) the exchange of heat and gas occur simultaneously in the same unit and thus decreases the priming volume of blood required to maintain the extra corporeal circulation.

In FIG. 3, there is shown in an exploded perspective view of the gas-heat exchanger 28, the first and second end plates 34 and 38 and the central gas-heat exchange portion 36.

As best shown in this view, the central gas-heat exchange portion 36 includes four coaxical cylinders, having their longitudinal axes coincident with each other extending between the first and second end plates 34 and 38, which are in the order of the center outwardly: (1) a solid screw member 58; (2) a plastic tubular right regular cylinder 60 immediately outside the screw member 58; (3) an aluminum right regular tubular cylinder 62 surrounding the plastic right regular tubular cylinder 60; and (4) a plastic right regular tubular cylinder 64 surrounding the aluminum right regular tubular cylinder 62. The plastic cylinders are formed of the plastic sold under the trademark Plexiglass.

To hold the gas-heat exchanger 28 together, the screw 58 includes a head 66 with a slot in it for threading at one end, and an elongated shank portion having external threads at the end opposite the head 66 for receiving and a wing nut 68. The head 66 fits outside the second end plate 38 and the wing nut 68 is threaded outside of the first end plate 34 to compress the end plates together against the central gas-heat exchange portion 36.

The aluminum right regular tubular cylinder 62 contains, within its center, the water compartment used to maintain the temperature. The plastic right regular tubular cylinder 60 within the compartment shields the screw 58 from the water used as a temperature control fluid. Both are sealed against the first and second end plates 34 and 38, with the interior of the aluminum right regular tubular cylinder 62 communicating with the source of temperature control fluid through the second tubular conduits 44A and 44B.

The space between the outer plastic right regular tubular cylinder 64 and the outer surface of the aluminum right regular tubular cylinder 62 forms the gas compartment and the gases communicate in this compartment through the first and second end plates 34 and 38 through the third tubular conduits 46A and 46B. The Silastic tubing is wound around the outside of the aluminum right regular tubular cylinder 62 which maintains its temperature while its surface is exposed to the gas in the gas compartment formed by the outer surface of the aluminum right regular tubular cylinder 62 and the inner surface of the plastic right regular tubular cylinder 64.

The silicone rubber tubing 40 has an outer diameter of approximately 3/32 inches, the plastic right regular tubular cylinder 60 has an outer diameter of one inch and an inner diameter of three-fourths of an inch, the aluminum right regular tubular cylinder 62 has an outer diameter of two inches and an inner diameter of one and seven-eighths of an inch and the outer plastic right regular tubular cylinder 64 has an outer diameter of two and one-half inches and an inner diameter of two and one-fourths of an inch in the preferred embodiment. The silicone rubber tubing 40 may be held in place at the ends or along the length by adhesive tape or the like.

To form a sealing connection, the first and second end plates 34 and 38 have within their inner surfaces three grooves indicated in the first end plate 34 at 69A, 70A and 72A numbering from the outer most ring to the inner most ring. Each of these recessed circles receives the end of a respective one of the cylinders 64, 62 and 60. To permit the threaded screw 58 to pass through the first and second end plates 34 and 38, each plate has an opening in its center indicated in first end plate 34 at 74A. The openings are recessed on the ends and sufficiently large to accommodate the screws without being so large as to extend outside the plastic right regular tubular cylinder 60.

The end plates in the preferred embodiment are approximately three and one-half inches by three and one-half inches by one-half inch although their dimensions are not critical as long as they are large enough to seal the tubes and permit entrance of the conduits.

To seal the tubular conduits 42A, 42B, 46A and 46B within the end plates, threaded fasteners 76A, 76B, 78A and 78B seal the tubular conduits 42A, 42B, 46A and 46B within their respective end plates. These seals are air tight and provide a gas tight gas compartment.

While plastic and aluminum tubes are used in the preferred embodiment, it is obvious that other kinds of tubes may be used. Silicone rubber has been found to be superior for containing liquid while permitting the exchange of gases but there are other materials known in the art, some of which may be suitable substitutes under some circumstances.

In FIG. 4, there is shown one of the fasteners 76A as it seals the first end plate 34. The others are substantially the same in structure.

The fastener 76A includes a cylindrical opening along its longitudinal axis which receives the tubular conduit 42A and which is aligned with an opening through the first end plate 34 to permit the tubular conduit 42A to pass therethrough. The fastener 76A includes an externally threaded portion 80 that fits within a tapped counterbore in the first end plate 34 having the threaded portion 80 ending on one end in a shoulder 82 and on the outer end with a head portion 84 larger than the threaded portion 80 to permit threading of the fastener 76A into the first end plate 34 with the tubular conduit 42A extending through it. An O-ring 86 is positioned within the counterbore against an annular end surface 88 thereof so that it abuts the outer wall of the tubular conduit 42A, the annular end surface 88 and the shoulder 82.

With this construction, the O-ring 86 is compressed against the annular end surface 88, the outer wall of the tubular conduit 42A and the shoulder 82 to seal the gas chamber of the lung 10 against the tubular conduit 42A, the first end plate 34 and the fastener 76A. This maintains a suitable gas tight chamber for the lung 10 while permitting easy assembly and disassembly.

From the above description it can be understood that the lung of this invention has several advantages, such as: (1) it is simple in construction and economical; (2) it is compact and small in size; (3) it combines the heat and gas exchanger in one unit; (4) it provides repeatable performance because the silicone rubber tubes are held in place and not susceptable to shifting in position; (5) it can be autoclaved and reused; (6) it may provide a superior exchange of gases such as oxygen and carbon dioxide; and (7) it provides good temperature control.

Although a preferred embodiment of the invention has been described with some particularity, many modifications and variations in the preferred embodiment are possible without deviating from the invention. Therefore, it is to be understood that, within the scope of the appended claims, the invention may be practiced other than as specifically described.

What is claimed is:

1. A method of gas-heat exchange with a perfusate comprising the steps of:
   causing the perfusate to flow along an elongated curved path around a heat exchanger, said path being at least partly defined by a membrane which is capable of passing gas to the perfusate and from the perfusate;
   controlling the temperature of the perfusate as it flows along the path and in contact with the membrane;
   transferring gas through the membrane while the temperature of the perfusate is being controlled and as it flows along the elongated curved path, the direction of the path of flow of the perfusate is changed while gas is being exchanged to cause mixing of the perfusate.

2. A method according to claim 1 in which the step of causing the perfusate to flow along an elongated curved path at least partly defined by a membrane includes the step of causing the perfusate to flow adjacent to a silicone rubber membrane along an elongated curved path.

3. A method according to claim 2 in which the step of causing the perfusate to flow along an elongated curved path at least partly defined by a membrane includes the step of causing the perfusate to flow through a tube formed of the membrane.

4. A method according to claim 3 in which the step of causing the perfusate to flow along an elongated curved path at least partly defined by a membrane includes the step of causing the flow of the perfusate to follow the path of a helix.

5. A method according to claim 4 in which the step of controlling the temperature of the perfusate includes the step of controlling its temperature as it flows through the helix.

6. A method according to claim 5 in which the step of causing a perfusate to flow along an elongated curved path at least partly defined by a membrane includes the step of causing blood to flow adjacent to a membrane.

7. A method according to claim 6 in which the step of transferring gas through the membrane includes the step of passing oxygen through the membrane into the perfusate.

8. A method according to claim 1 in which the step of causing the perfusate to flow along an elongated curved path at least partly defined by a membrane includes the step of causing the perfusate to flow through a tube formed of the membrane.

9. A method according to claim 8 in which the step of causing the perfusate to flow along an elongated curved path at least partly defined by a membrane includes the step of causing the flow of the perfusate to be in the path of a helix.

10. A method according to claim 9 in which the step of controlling the temperature of the perfusate includes the step of controlling its temperature as it flows through the path of the helix.

11. A method according to claim 10 in which the step of causing a perfusate to flow along an elongated curved path at least partly defined by a membrane includes the step of causing blood to flow adjacent to a membrane.

12. A method according to claim 11 in which the step of transferring gas through the membrane includes the step of passing oxygen through the membrane into the perfusate.

13. A method according to claim 1 in which the step of controlling the temperature of the perfusate includes the step of controlling its temperature as it flows through the path of the helix.

14. A method according to claim 13 in which the step of causing a perfusate to flow along an elongated curved step at least partly defined by a membrane includes the step of causing blood to flow adjacent to a membrane.

15. A method according to claim 14 in which the step of transferring gas through the membrane includes the step of passing oxygen through the membrane into the perfusate.

16. A method according to claim 1 in which the step of causing a perfusate to flow along an elongated curved path at least partly defined by a membrane includes the step of causing blood to flow adjacent to a membrane.

17. A method according to claim 16 in which the step of transferring gas through the membrane includes the step of passing oxygen through the membrane into the perfusate.

18. A method of gas-heat exchange with a perfusate comprising the steps of:

forcing blood through an elongated silicone rubber tube wound helically around a tube of good heat conducting material;

forcing oxygen through a compartment formed between the tube of good heat conducting material and a wall slightly above the helically-wound silicone rubber tube, whereby oxygen transfer is provided over a large portion of the surface area of the silicone tube; and forcing a cooling fluid through the tube of good heat conducting material, whereby heat is transferred from the blood in the silicone tube as it is forced through the silicone tube.

19. A method according to claim 18 in which the step of forcing a cooling fluid through said tube of good heat conducting material includes the step of forcing water at approximately 37 degrees Centigrade through the tube of good heat conducting material.

20. A method according to claim 19 in which the step of forcing blood through an elongated silicone rubber tube wound helically comprises the step of forcing blood through a silicone rubber tube having an outer diameter of approximately 3/32 of an inch and wound in a helix having an inner diameter of approximately two inches.

21. A method according to claim 20 in which the step of forcing oxygen through a compartment formed between the tube of good heat conducting material and a wall comprises the step of pumping oxygen through an annular compartment having an inner diameter of substantially two inches and an outer diameter of substantially two-and-one-half inches, with the oxygen passing between the wall having a diameter of two inches and the wall having a diameter of two-and-one-half inches.

* * * * *

UNITED STATES PATENT AND TRADEMARK OFFICE
CERTIFICATE OF CORRECTION

PATENT NO. : 4,306,018
DATED : December 15, 1981
INVENTOR(S) : Anthony F. Kirkpatrick It is certified that error appears in the above-identified patent and that said Letters Patent are hereby corrected as shown below:

Column 9, line 5, change "step" to --path--.

Signed and Sealed this

First Day of June 1982

[SEAL]

Attest:

GERALD J. MOSSINGHOFF

Attesting Officer     Commissioner of Patents and Trademarks